US008900640B2

(12) United States Patent
Shoji

(10) Patent No.: US 8,900,640 B2
(45) Date of Patent: Dec. 2, 2014

(54) EXPANDABLE, POROUS APATITE/COLLAGEN COMPOSITE, AND ITS PRODUCTION METHOD

(75) Inventor: Daisuke Shoji, Tokyo (JP)

(73) Assignee: Hoya Corporation, Tokyo (JP)

( * ) Notice: Subject to any disclaimer, the term of this patent is extended or adjusted under 35 U.S.C. 154(b) by 118 days.

(21) Appl. No.: 12/935,074

(22) PCT Filed: Mar. 17, 2009

(86) PCT No.: PCT/JP2009/055197

§ 371 (c)(1), (2), (4) Date: Sep. 28, 2010

(87) PCT Pub. No.: WO2009/122902

PCT Pub. Date: Oct. 8, 2009

(65) Prior Publication Data

US 2011/0014266 A1 Jan. 20, 2011

(30) Foreign Application Priority Data

Apr. 2, 2008 (JP) ................................ 2008-096050

(51) Int. Cl.

*A61K 33/42* (2006.01)
*A61P 19/08* (2006.01)
*A61K 9/00* (2006.01)
*A61L 27/46* (2006.01)
*A61L 27/56* (2006.01)

(52) U.S. Cl.

CPC *A61L 27/56* (2013.01); *A61L 27/46* (2013.01)
USPC .......................................... 424/602; 424/423

(58) Field of Classification Search

USPC .................................. 424/423, 602; 516/103
See application file for complete search history.

(56) References Cited

U.S. PATENT DOCUMENTS 5,571,181 A * 11/1996 Li ............................ 623/23.75
5,776,193 A 7/1998 Kwan et al.
7,153,938 B2 * 12/2006 Kikuchi et al. ............... 530/356
7,723,395 B2 * 5/2010 Ringeisen et al. ............. 521/50
7,732,573 B2 6/2010 Tanaka et al.
2005/0123581 A1 * 6/2005 Ringeisen et al. ............ 424/423
2006/0172918 A1 8/2006 Sotome et al.
2008/0234396 A1 * 9/2008 Shoji et al. .................... 516/103
2009/0149634 A1 6/2009 Shoji et al.
2009/0166580 A1 7/2009 Tanaka et al.
2010/0145468 A1 6/2010 Shoji
2010/0166828 A1 7/2010 Shoji
2010/0254900 A1 * 10/2010 Campbell et al. ............ 424/1.65

FOREIGN PATENT DOCUMENTS

EP 1 825 868 8/2007
WO 2003/035128 5/2003
WO 2006/046414 5/2006

OTHER PUBLICATIONS

Kikuchi et al. Glutaraldehyde cross-linked hydroxypatite/collagen self-oroganized nonocomposites, Biomaterials 25 (2004) 63-69.*
D. Bakos et al. Hydroxyapatite-collagen-hyaluronic acid composite, Biomaterials 20 (1999) 191-195.*
Kikuchi et al. Glutaraldehyde cross-linked hydroxyapatite/collagen self-organized nanocomposites, Biomaterials 25 (2004) 63-69.*
U.S. Appl. No. 12/989,107 to Daisuke Shoji, filed Oct. 22, 2010.
U.S. Appl. No. 12/990,566 to Daisuke Shoji, filed Nov. 1, 2010.
Yoshihiro Takenaka et al., "Apatite-Collagen Fukugotai no Kotsu Kesson Shufukuzai to shite no Oyo", The Japanese Society of Conservative Dentistry Gakujutsu Taikai Program Oyobi Koen Shorokushu, vol. 127, pp. 113.
M. Kikuchi et al., "Glutaraldehyde cross-linked hydroxyapatite/collagen self-organized nanocomposites", Biomaterials, vol. 25, , pp. 63-69, 2004.
D. Bakos et al., "Hydroxyapatite-collagen-hyaluronic acid composite", Biomaterials, vol. 20, No. 2, , pp. 191-195, 1999.

* cited by examiner

*Primary Examiner* — Anoop Singh
*Assistant Examiner* — Anna Falkowitz
(74) *Attorney, Agent, or Firm* — Greenblum & Bernstein, P.L.C.

(57) ABSTRACT

A expandable porous body constituted by a compressed apatite/collagen composite, which expands by water absorption, and a method for producing an expandable, porous apatite/collagen composite, which expands by water absorption, comprising the steps of freezing a porous apatite/collagen composite impregnated with a liquid in a compressed state, and drying it.

2 Claims, No Drawings

EXPANDABLE, POROUS APATITE/COLLAGEN COMPOSITE, AND ITS PRODUCTION METHOD

FIELD OF THE INVENTION

The present invention relates to a porous apatite/collagen composite usable as an artificial bone expanding (swelling) when implanted in the body, and its production method.

BACKGROUND OF THE INVENTION

Bone defect portions generated by bruise or illness are now treated by implanting patients' autogenous bones, similar bones provided by others, artificial bones made of metals such as titanium or hydroxyapatite ceramics, etc. Hydroxyapatite ceramics having bone conduction not achieved by conventional metals, polymers or alumina ceramics and directly bonding to bones have been gradually finding wider use as bone-repairing materials substituting autogenous bones in various fields such as oral surgery, neurological surgery, otorhinolaryngology, plastic surgery, etc., since their commercialization. However, artificial bones made of ceramics such as hydroxyapatite are hard and brittle, disadvantageous in difficulty in handling during operation. To solve such problems, apatite/collagen composites having sponge-like elasticity were developed for easy handling. However, filling bone defect portions having complicated shapes and different sizes is still difficult even with such materials, resulting in the likelihood of insufficient filling.

U.S. Pat. No. 5,776,193 discloses a porous, biodegradable, three-dimensionally fixed matrix for the replacement of bone comprising a bound network of water-insoluble, mineralized biopolymer (fixed phosphoric acid calcium) fibers, and a water-soluble binder (soluble collagen, etc.). However, this three-dimensionally fixed matrix fails to solve the above problems.

OBJECT OF THE INVENTION

Accordingly, an object of the present invention is to provide a porous apatite/collagen composite expandable when implanted as an artificial bone in the living body, and its production method.

DISCLOSURE OF THE INVENTION

As a result of intensive research in view of the above object, the inventor has found that a porous apatite/collagen composite freeze-dried in a compressed state can maintain the compressed state without releasing compressing strain, and that the porous body thus compressed can quickly return to a pre-compressed state by water absorption. The present invention has been completed based on such finding.

Thus, the porous apatite/collagen composite of the present invention is constituted by a compressed apatite/collagen composite, and expands by water absorption.

The volume change of the porous body by expansion by water absorption (volume after expansion/volume before expansion) is preferably 1.01 to 100 times.

The method of the present invention for producing an expandable, porous apatite/collagen composite, which expands by water absorption, comprises the steps of freezing a porous apatite/collagen composite impregnated with a liquid in a compressed state, and drying it.

The volume change ratio by compression (volume after compression/volume before compression) is preferably 1-99%.

DESCRIPTION OF THE BEST MODE OF THE INVENTION

[1] Expandable Porous Body of Apatite/Collagen Composite

The expandable porous body comprises a self-organized apatite/collagen composite and a binder such as collagen, etc., keeping a compressed state when it is dry, and expanding by water absorption to return to substantially a pre-compressed state. The porous body expanded by water absorption has the same elasticity as that of a usual porous apatite/collagen composite, as well as excellent biocompatibility and osteoconduction.

The volume change of the expandable porous body by expansion when immersed in water (volume after expansion/volume before expansion) is preferably 1.01-100 times, more preferably 1.1-60 times, most preferably 2-30 times. The volume change by expansion of less than 1.01 provides substantially no compression effect, while it is technically difficult to produce an expandable porous body expandable over 100 times.

The above properties owned by the porous bodies expandable by water absorption are preferable for biomaterials. Accordingly, the expandable porous bodies of the present invention can be used as substitution-type, bone-regenerating materials, etc. after sterilization with γ-rays, electron beams, dry heating, etc., specifically suitable for artificial bones, artificial joints, materials for connecting tendons to bones, dental implant materials, etc. The expandable porous bodies may be used in a compressed state or after expansion by water absorption. The expandable porous bodies may be in the form of blocks or granules.

[2] Production of Expandable, Porous, Apatite/Collagen Composite

The expandable porous body of the present invention can be obtained by compressing a porous body produced from an apatite/collagen composite and a binder such as collagen, etc. The apatite/collagen composite is preferably a composite similar to the living bone, in which hydroxyapatite and collagen are orientated in a self-organized manner. The term "self-organized" used herein means that calcium hydroxyphosphate having an apatite structure (hydroxyapatite) has orientation along collagen fibers, peculiar to the living bone; the C-axis of hydroxyapatite being orientated along collagen fibers.

(1) Production of Apatite/Collagen Composite (a) Starting Materials

The apatite/collagen composite is produced from collagen, a phosphate and a calcium salt. The collagen may be extracted from animals, etc., though their kinds, parts, ages, etc. are not particularly restrictive. In general, collagen obtained from skins, bones, cartilages, tendons, internal organs, etc. of mammals such as cow, pig, horse, rabbit and rat and birds such as hen, etc. may be used. Collagen-like proteins obtained from skins, bones, cartilages, fins, scales, internal organs, etc. of fish such as cod, flounder, flatfish, salmon, trout, tuna, mackerel, red snapper, sardine, shark, etc. may also be used. The extraction method of collagen is not particularly restrictive but may be a usual one. In place of collagen extracted from animal tissues, collagen produced by gene recombination technologies may also be used.

The phosphoric acid or its salt [hereinafter simply called "phosphoric acid (salt)"] may be phosphoric acid, disodium hydrogenphosphate, sodium dihydrogenphosphate, dipotassium hydrogenphosphate, potassium dihydrogenphosphate, etc. The calcium salts may be calcium carbonate, calcium acetate, calcium hydroxide, etc. The phosphoric acid (salt) and the calcium salt are preferably added in the form of a uniform aqueous solution or suspension.

The fiber length of the resultant apatite/collagen composite can be controlled by a mass ratio of the apatite-forming materials [phosphoric acid (salt) and calcium salt] to collagen used. Accordingly, the mass ratio of the apatite-forming materials to collagen is properly determined depending on a targeted formulation of the apatite/collagen composite. A mass ratio of apatite to collagen in the apatite/collagen composite used in the present invention is preferably 9/1 to 6/4, more preferably 8.5/1.5 to 7/3, most preferably 8/2.

(b) Preparation of Solution

An aqueous solution of collagen and phosphoric acid (salt) is generally prepared by adding an aqueous collagen solution to an aqueous phosphoric acid (salt) solution. The concentration of collagen in the aqueous solution of collagen and phosphoric acid (salt) is preferably 0.1-1.5% by mass, particularly about 0.85% by mass. The concentration of phosphoric acid (salt) is preferably 15-240 mM, particularly about 120 mM. The aqueous collagen solution used preferably contains about 0.85% by mass of collagen and about 20 mM of phosphoric acid. The concentration of an aqueous calcium salt solution (or suspension) is preferably 50-800 mM, particularly about 400 mM.

(c) Synthesis Method

An aqueous solution of collagen and phosphoric acid (salt), and an aqueous calcium salt solution or suspension are simultaneously dropped into water substantially in the same amount as that of the aqueous calcium salt solution or suspension added at about 40° C. to form an apatite/collagen composite. The fiber length of the synthesized apatite/collagen composite can be controlled by adjusting dropping conditions such as a dropping speed, a stirring speed, a temperature, etc. The dropping speed is preferably 1 to 60 mL/minute, more preferably about 30 mL/minute. The stirring speed is preferably 1 to 400 rpm, more preferably about 200 rpm. The mixing ratio of the phosphoric acid (salt) to the calcium salt is preferably 1/1 to 2/5, more preferably about 3/5. The mixing ratio of collagen to apatite (the total of the phosphoric acid salt and the calcium salt) is preferably 1/9 to 4/6, more preferably 1.5/8.5 to 3/7.

The reaction solution is preferably kept at pH of 8.9 to 9.1 by maintaining a calcium ion concentration at 3.75 mM or less and a phosphoric acid ion concentration at 2.25 mM or less in the reaction solution. Outside the above concentration ranges of the calcium ion and/or the phosphoric acid ion, the self-organization of the composite would be hindered. The above dropping conditions provide the self-organized apatite/collagen composite with fiber length of 2 mm or less suitable as a powdery apatite/collagen material.

After the completion of dropping, a slurry-like, aqueous apatite/collagen composite dispersion is freeze-dried. The freeze-drying is carried out by rapidly drying in vacuum in a frozen state at −10° C. or lower.

(2) Production of Expandable, Porous Apatite/Collagen Composite (a) Preparation of Apatite/collagen Composite Dispersion The apatite/collagen composite powder is mixed with water, an aqueous phosphoric acid solution, etc., and stirred to prepare a paste-like dispersion (slurry). The amount of water in the dispersion is preferably 80 to 99% by volume, more preferably 90 to 97% by volume. The porosity P (%) of the porous body depending on a volume ratio of the apatite/collagen composite to the aqueous solution, etc. in the dispersion is represented by the following formula (1):

$$P=B/(A+B)\times 100 \quad (1),$$

wherein A represents the volume of the apatite/collagen composite in the dispersion, and B represents the volume of a liquid in the dispersion. Accordingly, it is possible to control the porosity P of the porous body by adjusting the amount of the liquid added. Apatite/collagen composite fibers are partially cut by stirring the dispersion after adding the liquid, resulting in a larger fiber length distribution range, and thus providing the resultant porous body with improved strength.

To provide the porous composite with shape stability, a binder is preferably added to the dispersion. The binders may be soluble collagen, gelatin, polylactic acid, polyglycolic acid, copolymers of lactic acid and glycolic acid, polycaprolactone, carboxymethylcellulose, cellulose esters, dextrose, dextran, chitosan, hyaluronic acid, Ficoll, chondroitin sulfate, polyvinyl alcohol, polyacrylic acid, polyethylene glycol, polypropylene glycol, water-soluble polyacrylate, water-soluble polymethacrylate, etc., and the soluble collagen is particularly preferable. The amount of the binder added is preferably 1-10% by mass, more preferably 3-6% by mass, based on 100% by mass of the apatite/collagen composite.

As in the production of the apatite/collagen composite, the binder is added preferably in the form of an aqueous phosphoric acid solution. The concentration, etc. of the binder solution added are not particularly restrictive, but practically the concentration of the binder is preferably about 0.85% by mass, and the concentration of the phosphoric acid is preferably about 20 mM.

To prevent collagen from becoming gelatin in the gelation described later, the binder-added dispersion is adjusted to have pH of about 7, preferably 6.8-7.6, more preferably 7.0-7.4. The adjustment of the pH is preferably conducted by an aqueous sodium hydroxide solution.

When collagen is added as a binder to accelerate the collagen to become fibers, the dispersion is mixed with a concentrated (about 10 times) solution of a physiological buffer saline (PBS) of phosphoric acid to adjust the ionic strength of the dispersion to 0.2 to 1. The more preferred ionic strength is as large as about 0.8, on the same level as that of PBS.

Additives such as antibiotics (tetracycline, etc.), chemotherapeutic agents (cisplatin, etc.), bone marrow cells, cell-proliferating factors (BMP, FGF, TGF-β, IGF, PDGF, VEGF, etc.), physiological activation factors (hormone, cytokine, etc.), etc. may be added to the dispersion within a range not hindering the object of the present invention.

(b) Gelation of Dispersion

The dispersion charged into a molding die is kept at a temperature of 35-45° C. to turn collagen in the dispersion to fibers, thereby gelating the dispersion. Gelation prevents the apatite/collagen composite from precipitating, thereby producing a uniform porous body. The heating temperature is more preferably 35-40° C., and the heating time is preferably 0.5-3.5 hours, more preferably 1-3 hours.

(c) Freeze Drying

After the gelation, the dispersion is frozen for drying to obtain a porous body. the freezing temperature is preferably −80° C. to −10° C., more preferably −80° C. to −20° C. The sizes and shapes of pores in the porous body can be controlled by a freezing speed. For instance, a larger freezing speed tends to provide smaller pore sizes to the resultant porous body.

The freeze-drying is carried out by evacuating and rapidly drying in a frozen state at −10° C. or lower, as in the case of the composite. As long as the dispersion is sufficiently dried, the freeze-drying time is not particularly restricted, but generally about 24 to 72 hours.

(d) Cross-Linking of Collagen

To provide artificial bones, etc. with increased mechanical strength and shape retention for a desired period of time when implanted in a human body, it is preferable to cross-link collagen in the freeze-dried apatite/collagen composite. The cross-linking of collagen may be carried out by any methods such as physical cross-linking methods using γ-rays, ultraviolet rays, electron beams, thermal dehydration, etc., or chemical cross-linking methods using cross-linking agents, condensation agents, etc. The chemical cross-linking can be conducted, for instance, by a method of immersing the freeze-dried porous body in a cross-linking agent solution, a method of bringing the freeze-dried porous body into contact with a steam containing a cross-linking agent, or a method of adding a cross-linking agent to an aqueous solution or suspension of the apatite/collagen composite in the course of its production process.

The cross-linking agents may be aldehydes such as glutaraldehyde, formaldehyde, etc.; isocyanates such as hexamethylene diisocyanate, etc.; carbodiimides such as a hydrochloric acid salt of 1-ethyl-3-(3-dimethylaminopropyl) carbodiimide; epoxies such as ethylene glycol diethyl ether, etc.; transglutaminase, etc. Among these cross-linking agents, glutaraldehyde is particularly preferable from the aspects of the easiness of controlling the degree of cross-linking and the compatibility of the cross-linked, apatite/collagen porous body with a human body.

When the porous body is immersed in a glutaraldehyde solution for cross-linking, the concentration of the glutaraldehyde solution is preferably 0.005 to 0.015% by mass, more preferably 0.005 to 0.01% by mass. When an alcohol such as ethanol is used as a solvent for glutaraldehyde, dehydration occurs simultaneously with the cross-linking of collagen. Accordingly, a cross-linking reaction occurs in a state where the apatite/collagen composite is contracted, resulting in a cross-linked, apatite/collagen porous body with improved elasticity.

After the cross-linking, the porous body is immersed in and washed with an aqueous solution of about 2% by mass of glycine to remove unreacted glutaraldehyde, and then washed with water. It is further immersed in ethanol for dehydration, and then dried at room temperature.

(e) Working

The cross-linked, apatite/collagen porous body is worked by machining by a lathe, etc., if necessary. The apatite/collagen porous body may be worked after compression described later.

(f) Pressing of Porous Body

The porous body impregnated with water by immersion in a liquid such as a physiological saline solution, etc. is frozen under desired pressure, and dried to form an expandable porous body. The freeze drying can be conducted in the same manner as described above. When no working is conducted, the cross-linked porous body may be directly compressed without drying. Pressure may be applied to a porous block body put in a die open in only one surface, using a compressing die inserted into the die through the open surface, etc., or a rubber press. When compression and freeze drying are conducted simultaneously, the compressing die, etc. preferably have vents to make water escape from the porous body.

By adjusting the strength and direction of pressure applied to the porous body, it is possible to control the expansion ratio of the expandable porous body. The volume change ratio by compression (volume after compression/volume before compression) is preferably 1-99%. When this volume change ratio is more than 99%, substantially no compression effect is obtained. On the other hand, when pressure is applied such that the volume change ratio is less than 1%, fibers in the apatite/collagen composite are damaged, resulting in an extremely reduced expansion ratio. The volume change ratio by compression is more preferably 5-95%, further preferably 10-90%. The freeze-dried porous body may be sterilized with ultraviolet rays, γ-rays, electron beams, dry-heating, etc.

The present invention will be explained in more detail referring to Examples below without intention of restricting it thereto.

Example 1

(1) Production of Apatite/Collagen Composite 400 ml of a 120-mM aqueous phosphoric acid solution was added to 412 g of aqueous collagen solution containing phosphoric acid (0.97% by weight of collagen, and 20 mM of phosphoric acid) to obtain a solution I. 400 ml of a 400-mM calcium hydroxide solution (solution II) was also prepared. Both solutions I and II were simultaneously dropped into 200 ml of water (39.5° C.) to obtain a apatite/collagen composite slurry. Incidentally, the solutions I and II were dropped while stirring a reaction solution at 200 rpm. The dropping speed was adjusted to about 30 mL/min such that the reaction solution was kept at pH of 8.9-9.1. The fiber length of the resultant apatite/collagen composite was about 2 mm or less. The slurry was freeze-dried. The mass ratio of apatite to collagen in the composite was 8/2.

(2) Production of Porous Apatite/Collagen Composite 1 g of the dried apatite/collagen composite was added to 3.6 ml of pure water and stirred to form a paste-like dispersion. This paste-like dispersion was mixed with 4 g of an aqueous collagen solution containing phosphoric acid and stirred, and a 1-N aqueous NaOH solution was added until the pH reached about 7. A mass ratio of the apatite/collagen composite to collagen was 97/3. Tenfold-concentrated PBS was then added to the dispersion until the ionic strength of the dispersion reached 0.8. The amount of a liquid (pure water, aqueous phosphoric acid solution, aqueous NaOH solution, and PBS) in the dispersion was 95% by volume.

The dispersion was charged into a molding die and kept at 37° C. for 2 hours for gelation to obtain a jelly-like formed body. This formed body was frozen at −20° C., and then dried by a freeze dryer. The dried formed body was immersed in a solution of 0.01% of glutaraldehyde in ethanol (concentration: 99.5%), and cross-linked to obtain a porous body. After washed with water, this porous body was immersed in a 2-% aqueous glycine solution to remove unreacted glutaraldehyde, and then washed with water again. It was further immersed in ethanol (concentration: 99.5%) for dehydration, and then dried at room temperature.

The porous body was formed into a cubic body (10 mm×10 mm×10 mm), immersed in a physiological saline solution so that it was fully impregnated with water, compressed in one direction in a die such that a ratio of (volume after compression/volume before compression) was 20%, and frozen in the compressed state. When compression was stopped in the frozen state, the porous body kept a compressed shape. This porous body in the frozen state was dried by a freeze drier, and sterilized with γ-rays to obtain the expandable porous body of the present invention of 2 mm×10 mm×10 mm.

When the expandable porous body was immersed in a physiological saline solution, it expanded to a shape of 9 mm×10 mm×10 mm.

Effect of the Invention

The expandable, porous apatite/collagen composites of the present invention can be implanted with low invasion in bone defect portions having complicated shapes and different sizes without insufficient filling. Because the expandable porous body has a relatively small size before expansion, it can easily be implanted in a hole with a small opening. Burden is reduced for a patient having this expandable porous body implanted as an artificial bone, and because the artificial bone need not be worked for implanting, a doctor can conduct operation easily by using it.

The present disclosure relates to subject matter contained in Japanese Patent Application No. 2008-096050 filed on Apr. 2, 2008, which is expressly incorporated herein by reference in its entirety.

What is claimed is:

1. A method for producing an expandable, dry porous apatite/collagen composite, which expands by water absorption to return to a precompressed state, comprising compressing a porous apatite/collagen composite impregnated with a liquid;

freezing the compressed porous apatite/collagen composite;

stopping the compression; and drying the compressed porous apatite/collagen composite, wherein the freezing and the compressing of the porous apatite/collagen composite occurs simultaneously; and wherein the composite maintains a compressed shape when dry.

2. The method for producing an expandable porous body according to claim 1, wherein the volume change ratio by compression (volume after compression/volume before compression) is 1-99%.

* * * * *